(12) United States Patent
Takahashi

(10) Patent No.: US 10,776,853 B2
(45) Date of Patent: Sep. 15, 2020

(54) BEDDING ITEM SELECTION SYSTEM AND BEDDING ITEM PHYSICAL PROPERTY RECOGNITION SYSTEM

(71) Applicant: EMOOR Co., Ltd., Tachikawa-shi, Tokyo (JP)

(72) Inventor: Koji Takahashi, Tokyo (JP)

(73) Assignee: EMOOR CO., LTD., Tokyo (JP)

( * ) Notice: Subject to any disclaimer, the term of this patent is extended or adjusted under 35 U.S.C. 154(b) by 242 days.

(21) Appl. No.: 15/576,171

(22) PCT Filed: Dec. 2, 2016

(86) PCT No.: PCT/JP2016/085950
§ 371 (c)(1),
(2) Date: Nov. 21, 2017

(87) PCT Pub. No.: WO2017/104451
PCT Pub. Date: Jun. 22, 2017

(65) Prior Publication Data
US 2018/0137554 A1 May 17, 2018

(30) Foreign Application Priority Data
Dec. 16, 2015 (JP) .................. 2015-245250

(51) Int. Cl.
*G06Q 30/00* (2012.01)
*G06Q 30/06* (2012.01)
(Continued)

(52) U.S. Cl.
CPC ....... *G06Q 30/0631* (2013.01); *A47G 9/0238* (2013.01); *A61B 5/4806* (2013.01);
(Continued)

(58) Field of Classification Search
CPC ............... G06Q 30/06; G06Q 30/0269; G06Q 30/0631; G06Q 50/22; A61B 5/4806;
(Continued)

(56) References Cited

U.S. PATENT DOCUMENTS 6,571,192 B1 * 5/2003 Hinshaw ............... A47C 31/123
702/129
6,741,950 B2 * 5/2004 Hinshaw ............... A47C 31/123
702/129
(Continued)

FOREIGN PATENT DOCUMENTS

JP 2001-299545 10/2001
JP 2003-216734 7/2003
(Continued)

OTHER PUBLICATIONS

Jung-Yong Kim et al. "Measurement of User Experience to Select a Comfortable Mattress" A. Marcus (Ed.): Design, User Experience, and Usability, Pt II, HCII 2011, LNCS 6770, pp. 449-458, 2011 © Springer-Verlag Berlin Heidelberg 2011. ISSN 0302-9743, ISBN 978-3-642-21707-4 (Year: 2011).*
(Continued)

*Primary Examiner* — Naeem U Haq
(74) *Attorney, Agent, or Firm* — Rankin, Hill & Clark LLP

(57) ABSTRACT

There is provided a bedding item selection system capable of selecting a bedding item easy to improve the state of sleep. A bedding item selection system S1 includes: a plurality of test bedding items T whose physical property including firmness is different from one another; a deep sleep rate calculation unit 1*f* which calculates a deep sleep rate of a user P based on biological information measured and recorded; a suitable physical property recognition unit 1*h* which recognize a suitable physical property based on the physical property of a test bedding item T high in deep sleep
(Continued)

rate of the user P; and a bedding item selection unit 1j which selects, from a plurality of selectable bedding items M, a bedding item based on the suitable physical property.

6 Claims, 8 Drawing Sheets

(51) Int. Cl.
*G06Q 50/22* (2018.01)
*G06Q 30/02* (2012.01)
*A47G 9/02* (2006.01)
*A61B 5/00* (2006.01)
*A47G 9/10* (2006.01)

(52) U.S. Cl.
CPC ......... *G06Q 30/0269* (2013.01); *G06Q 30/06* (2013.01); *G06Q 50/22* (2013.01); *A47G 9/10* (2013.01); *A61B 5/4815* (2013.01); *A61B 2503/12* (2013.01)

(58) Field of Classification Search
CPC .............. A61B 5/4815; A61B 2503/12; A47G 9/0238; A47G 9/10
See application file for complete search history.

(56) References Cited

U.S. PATENT DOCUMENTS

| | | | | |
|---|---|---|---|---|
| 6,990,425 B2* | 1/2006 | Hinshaw | ............... | A47C 31/123 702/129 |
| 7,937,238 B2* | 5/2011 | Boyd | ................... | A47C 31/123 702/127 |
| 8,458,042 B1* | 6/2013 | Roberts | ................ | A47C 31/123 705/26.1 |
| 8,676,662 B1 | 3/2014 | Roberts et al. | | |
| 9,592,005 B2* | 3/2017 | Oakhill | ................... | G16H 50/30 |
| 9,592,006 B2* | 3/2017 | Oakhill | ................... | G16H 50/30 |
| 9,659,322 B2* | 5/2017 | Gorjanc | ............ | G06Q 30/0631 |
| 9,833,188 B2* | 12/2017 | Oakhill | ................... | G16H 50/30 |
| 9,895,010 B1* | 2/2018 | Alletto, Jr. | ............... | G09F 23/00 |
| 2009/0006027 A1* | 1/2009 | Hinshaw | ............... | A47C 31/123 702/129 |
| 2010/0317930 A1* | 12/2010 | Oexman | ............... | A47C 31/123 600/300 |
| 2011/0224510 A1* | 9/2011 | Oakhill | ................... | G16H 50/30 600/301 |
| 2015/0320354 A1 | 11/2015 | Oakhill | | |
| 2016/0260362 A1* | 9/2016 | Alletto | ..................... | G09F 23/00 |
| 2016/0345746 A1* | 12/2016 | Myers | ................... | A47C 31/123 |
| 2017/0202366 A1* | 7/2017 | Mackey | ................ | A47C 31/123 |

FOREIGN PATENT DOCUMENTS

| | | |
|---|---|---|
| JP | 2004-514515 | 5/2004 |
| WO | 2012/012892 | 2/2012 |

OTHER PUBLICATIONS

International Search Report, dated Dec. 27, 2016 (dated Dec. 27, 2016), 2 pages.
European Search Report dated Apr. 25, 2019, 9 pages.

* cited by examiner

FIG.3

NAME  TARO  YAMADA   Mr/Ms

SEX  ● MALE   ○ FEMALE

AGE  40s ▽

HEIGHT  163  cm

WEIGHT  50  kg

FIG.4

| HEIGHT DATA | | | |
|---|---|---|---|
| SEX: MALE | AGE: 40s | TARGET SITE: HIP | |

| BMI | FIRMNESS | AVERAGE DEEP SLEEP RATE | AVERAGE DEGREE OF SOUND SLEEP |
|---|---|---|---|
| 15 | 100-130 | 55 | 3.60 |
| 16 | | 62 | 4.78 |
| 17 | | 78 | 3.55 |
| 18 | | 60 | 2.24 |
| 19 | 110-140 | 48 | 1.86 |
| 20 | | 44 | 2.36 |
| 21 | | 49 | 3.15 |
| 22 | | 52 | 4.59 |
| 23 | | 58 | 4.83 |
| 24 | | 70 | 4.11 |
| 25 | | 62 | 3.56 |
| 26 | 130-160 | 54 | 3.02 |
| 27 | | 50 | 2.87 |
| 28 | | 42 | 3.65 |
| 29 | | 51 | 3.55 |
| 30 | | 59 | 3.79 |
| 31 | | 62 | 3.92 |
| 32 | | 67 | 4.40 |

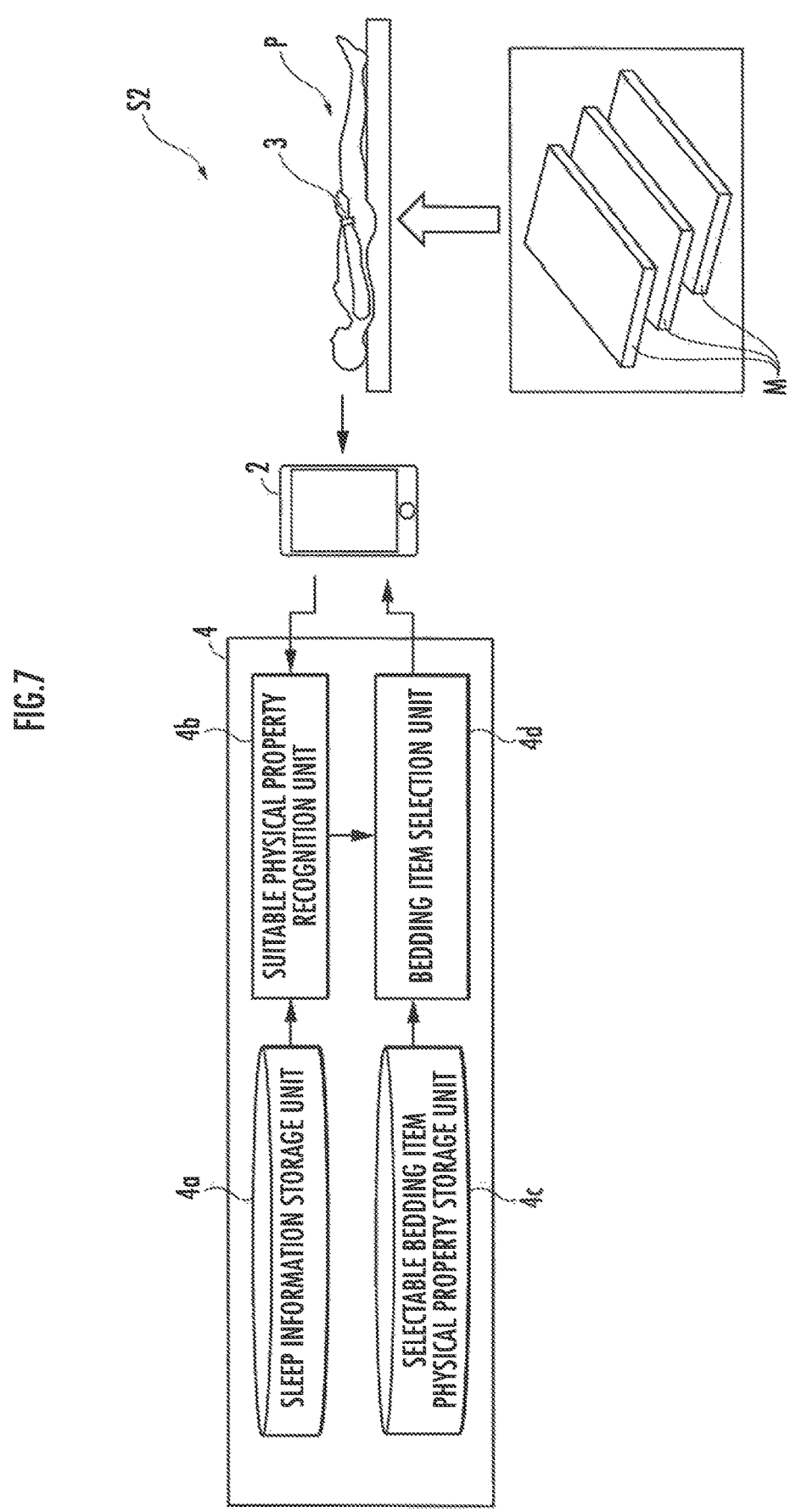

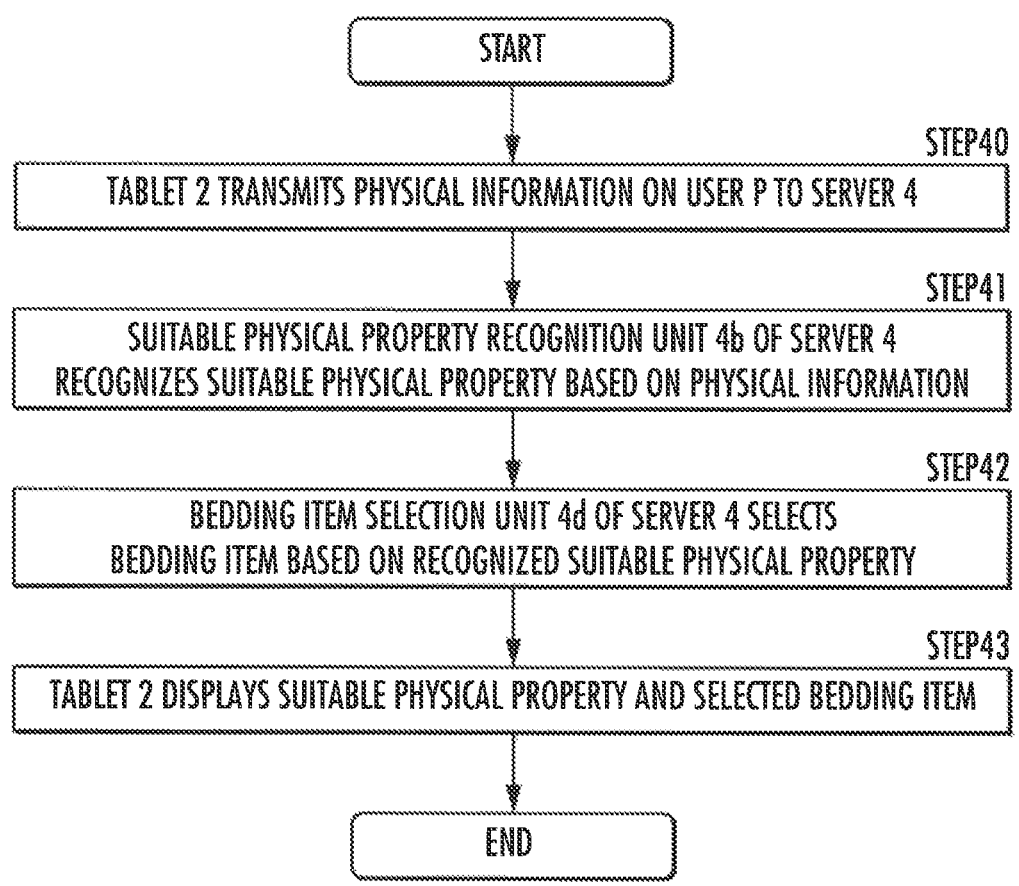

BEDDING ITEM SELECTION SYSTEM AND BEDDING ITEM PHYSICAL PROPERTY RECOGNITION SYSTEM

TECHNICAL FIELD

The present invention relates to a bedding item selection system configured to select a bedding item, which is likely to improve the state of user's sleep, from multiple selectable bedding items, and a bedding item physical property recognition system configured to recognize the physical properties of a bedding item which is likely to improve the state of user's sleep.

BACKGROUND ART

Conventionally, there has been known a sleep evaluation system configured to ask a user multiple questions, and evaluate the state of sleep based on the answers. In this type of sleep evaluation system, there is a system configured to select, from multiple selectable bedding items, a bedding item as being suitable for the user based on the evaluation results (for example, see Patent Literature 1).

CITATION LIST

Patent Literature

Patent Literature 1: Japanese Patent Application Laid-Open No. 2003-216734

SUMMARY OF INVENTION

Technical Problem

In the meantime, in a conventional sleep evaluation system as described in Patent Literature 1, the state of sleep is evaluated based on user's subjective data as the answers to the questions. Therefore, it cannot be said that the content of evaluation by the conventional sleep evaluation system objectively sees the state of sleep of each individual user.

Further, commercial products to be selected based on the evaluation are selected by respective systems based on respective unique criteria, which include many commercial products having no support to improve the state of sleep.

As a result, a bedding item selected based on the evaluation by the conventional sleep evaluation system does not often correspond to the actual state of user's sleep. Thus, there is a problem that it is difficult for the bedding item selected using the conventional sleep evaluation system to improve the state of sleep in a practical sense.

The present invention has been made in view of the above points, and it is an object thereof to provide a bedding item selection system capable of selecting a bedding item which is likely to improve the state of sleep, and a bedding item physical property recognition system capable of recognizing the physical properties of a bedding item which is likely to improve the state of sleep.

Solution to Problem

A first aspect of the invention in this application is an invention related to a bedding item selection system configured to recognize the physical property of a bedding item high in deep sleep rate based on the deep sleep rate of a user during sleep on a test bedding item, and to select a bedding item based on the recognized physical property.

A second aspect of the invention in this application is an invention related to a bedding item selection system configured to recognize the physical property of a bedding item high in degree of sound sleep based on a degree of sound sleep entered by a user after sleep on a test bedding item, and select a bedding item based on the recognized physical property.

A third aspect of the invention in this application is an invention related to a bedding item selection system configured to recognize the physical property of a bedding item high in deep sleep rate based on user's physical information entered, and correlation data among the deep sleep rate, the physical property of the bedding item, and the physical information, which are collected in advance, and to select a bedding item based on the recognized physical property.

A fourth aspect of the invention in this application is an invention related to a bedding item selection system configured to recognize the physical property of a bedding item high in degree of sound sleep based on user's physical information entered, and correlation data among the degree of sound sleep, the physical property of the bedding item, and the physical information, which are collected in advance, and to select a bedding item based on the recognized physical property.

A fifth aspect of the invention in this application is an invention related to a bedding item physical property recognition system configured to recognize the physical property of a bedding item high in deep sleep rate based on the deep sleep rate of a user during sleep on a test bedding item.

A sixth aspect of the invention in this application is an invention related to a bedding item physical property recognition system configured to recognize the physical property of a bedding item high in degree of sound sleep based on the degree of sound sleep entered by a user after sleep on a test bedding item.

A seventh aspect of the invention in this application is an invention related to a bedding item physical property recognition system configured to recognize the physical property of a bedding item high in deep sleep rate based on user's physical information entered, and correlation data among the deep sleep rate, the physical property of the bedding item, and the physical information, which are collected in advance.

An eighth aspect of the invention in this application is an invention related to a bedding item physical property recognition system configured to recognize the physical property of a bedding item high in degree of sound sleep based on user's physical information entered, and correlation data among the degree of sound sleep, the physical property of the bedding item, and the physical information, which are collected in advance.

The first aspect of the invention to the eighth aspect of the invention will be described in detail below.

The bedding item selection system of the first aspect of the invention is a bedding item selection system configured to select a bedding item from multiple selectable bedding items, including: multiple test bedding items whose physical property including firmness is different from one another; a selectable bedding item physical property storage unit which stores each of the physical properties for each of the selectable bedding items; a test bedding item physical property storage unit which stores the physical property for each of the test bedding items; a biological information measurement unit which measures biological information on a user during sleep on the test bedding item; a biological information recording unit which records the biological information measured by the biological information measurement unit; a deep sleep rate calculation unit which calculates a deep sleep rate of the user based on the recorded biological information; a suitable bedding item recognition unit which compares the deep sleep rate calculated for each of the test bedding items to recognize, as a suitable bedding item, the test bedding item high in the deep sleep rate of the user; a suitable physical property recognition unit which recognizes, as a suitable physical property, a physical property high in the deep sleep rate of the user based on the test bedding item recognized as the suitable bedding item by the suitable bedding item recognition unit and the physical property stored in the test bedding item physical property storage unit; and a bedding item selection unit which selects, from the multiples electable bedding items, a bedding item high in the deep sleep rate of the user based on the physical property recognized as the suitable physical property by the suitable physical property recognition unit and the physical property stored in the selectable bedding item physical property storage unit.

Thus, in the bedding item selection system of the present invention, the user first tries experimental sleeping on a test bedding item whose physical property is obtained in advance. Here, the physical property includes firmness which is easy to measure and strongly influences the body movement (i.e., the state of sleep).

Then, based on the biological information measured by the biological information measurement unit during experimental sleep and recorded by the biological information recording unit, the deep sleep rate calculation unit calculates a deep sleep rate of the user for each test bedding item. Next, based on the deep sleep rate, the suitable bedding item recognition unit recognizes, as a suitable bedding item, the test bedding item high in the deep sleep rate of the user. Next, based on the test bedding item recognized as the suitable bedding item, the suitable physical property recognition unit recognizes, as a suitable physical property, the physical property high in the deep sleep rate of the user. Finally, based on the physical property recognized as the suitable physical property, the bedding item selection unit selects a bedding item.

In other words, in the bedding item selection system of the present invention, the deep sleep rate obtained based on personal biological information on the user, and the physical property including the firmness, which is easy to measure and strongly influences the state of sleep, are used in selecting a bedding item. Therefore, according to the bedding item selection system of the present invention, since a bedding item can be selected while reflecting the sleep information as the deep sleep rate acquired for each user in the physical property which objectively influences the sleep, a bedding item easy to improve the state of sleep can be selected.

It is preferred that the bedding item selection system of the first aspect of the invention should further include: a degree-of-sound-sleep input unit to which a degree of sound sleep the user feels after sleep on the test bedding item is input, wherein the suitable bedding item recognition unit compares the deep sleep rate calculated for each of the test bedding items and the input degree of sound sleep to recognize, as the suitable bedding item, the test bedding item high in the deep sleep rate and the degree of sound sleep of the user, the suitable physical property recognition unit recognizes, as the suitable physical property, the physical property high in the deep sleep rate and the degree of sound sleep of the user based on the test bedding item recognized as the suitable bedding item by the suitable bedding item recognition unit and the physical property stored in the test bedding item physical property storage unit, and the bedding item selection unit selects, from the multiple selectable bedding items, a bedding item high in the deep sleep rate and the degree of sound sleep of the user.

Thus, when a bedding item is selected by referring to subjective sleep information as the degree of sound sleep the user feels as well as objective sleep information as the deep sleep rate based on the biological information on the user, it is easy to select a bedding item suitable for the user. As a result, it is easier to select a bedding item easy to improve the state of sleep.

It is also preferred that the bedding item selection system of the first aspect of the invention should further include: a physical information input unit to which physical information including height and weight of the user is input; a sleep information storage unit which stores correlation data among the physical property, the deep sleep rate, and the physical information, which are collected in advance; a test physical property recognition unit which recognizes, as a test physical property, test physical property which is likely to increase the deep sleep rate of the user based on the input physical information and the correlation data stored in the sleep information storage unit; and a test bedding item selection unit which selects, from the multiple test bedding items, the test bedding item which is likely to increase the deep sleep rate of the user based on the physical property recognized as the test physical property by the test physical property recognition unit, and the physical property stored in the test bedding item physical property storage unit.

Thus, when the test bedding item is selected based on user's physical information input to the physical information input unit, and the correlation data among the physical property, the deep sleep rate, and the physical information, which are stored in the sleep information storage unit, it is easy to select the test bedding item which is likely to increase the deep sleep rate of the user.

As a result, since it is easy for the suitable bedding item recognition unit to recognize, as a suitable bedding item, the test bedding item high in deep sleep rate without repeating experimental sleeping using test bedding items many times (i.e., this makes it easier to obtain a physical property which is likely to be able to improve the state of sleep), it is easier to select a bedding item easy to improve the state of sleep.

It is further preferred that the bedding item selection system of the first aspect of the invention should be such that, when a test bedding item to be used is selected based on correlation data among the physical property, the deep sleep rate, and the physical information; which are stored in the sleep information storage unit, the sleep information storage unit stores the deep sleep rate calculated by the deep sleep rate calculation unit, the physical information on the user whose deep sleep rate is calculated, and the physical property of the test bedding item used by the user.

Thus, when data used in selecting a bedding item are accumulated, it is easy to select a suitable test bedding item from the beginning next time the bedding item selection system is used. As a result, it is easier to select a bedding item easy to further improve the state of sleep.

The bedding item selection system of the second aspect of the invention is a bedding item selection system configured to select a bedding item from a plurality of selectable bedding items, including: multiple test bedding items whose physical property including firmness is different from one another; a selectable bedding item physical property storage unit which stores the physical property for each of the selectable bedding items; a test bedding item physical property storage unit which stores the physical property for each of the test bedding items; a degree-of-sound-sleep input unit to which a degree of sound sleep a user feels after sleep on the test bedding item is input; a suitable bedding item recognition unit which compares the degree of sound sleep input for each of the test bedding items to recognize, as a suitable bedding item, the test bedding item high in the degree of sound sleep of the user; a suitable physical property recognition unit which recognizes, as a suitable physical property, a physical property high in the degree of sound sleep of the user based on the test bedding item recognized as the suitable bedding item by the suitable bedding item recognition unit and the physical property stored in the test bedding item physical property storage unit; and a bedding item selection unit which selects, front the multiple selectable bedding items, a bedding item high in the degree of sound sleep of the user based on the physical property recognized as the suitable physical property by the suitable physical property recognition unit and the physical property stored in the selectable bedding item physical property storage unit.

Thus, in the bedding item selection system of the present invention, the user first tries experimental sleeping on a test bedding item whose physical property is obtained in advance. Here, the physical property includes firmness which is easy to measure and strongly influences the body movement (i.e., the state of sleep).

Then, a degree of sound sleep the user feels after the experimental sleep is input to the degree-of-sound-sleep input unit. Next, based on the degree of sound sleep, the suitable bedding item recognition unit recognizes, as a suitable bedding item, the test bedding item high in the degree of sound sleep of the user. Next, based on the test bedding item recognized as the suitable bedding item, the suitable physical property recognition unit recognizes, as a suitable physical property, the physical property high in the degree of sound sleep of the user. Finally, based on the physical property recognized as the suitable physical property, the bedding item selection unit selects a bedding item.

In other words, in the bedding item selection system of the present invention, the degree of sound sleep entered by the user, and the physical property including the firmness, which is easy to measure and strongly influences the state of sleep, are used in selecting a bedding item. Therefore, according to the bedding item selection system of the present invention, since a bedding item can be selected while reflecting the sleep information as the degree of sound sleep acquired for each user in the physical property which objectively influences the sleep, a bedding item easy to improve the state of sleep can be selected.

It is preferred that the bedding item selection system of the second aspect of the invention should further include: a biological information measurement unit which measures biological information on a user during sleep on the test bedding item; a biological information recording unit which records the biological information measured by the biological information measurement unit; and a deep sleep rate calculation unit which calculates a deep sleep rate of the user based on the recorded biological information, wherein the suitable bedding item recognition unit compares the deep sleep rate calculated for each of the test bedding items and the input degree of sound sleep to recognize, as the suitable bedding item, the test bedding item high in the deep sleep rate and the degree of sound sleep of the user, the suitable physical property recognition unit recognizes, as the suitable physical property, the physical property high in the deep sleep rate and the degree of sound sleep of the user based on the test bedding item recognized as the suitable bedding item by the suitable bedding item recognition unit, and the physical property stored in the test bedding item physical property storage unit, and the bedding item selection unit selects, from the multiple selectable bedding items, a bedding item high in the deep sleep rate and the degree of sound sleep of the user.

Thus, when a bedding item is selected by referring to objective sleep information as the deep sleep rate based on the biological information on the user as well as subjective sleep information as the degree of sound sleep the user feels; it is easy to select a bedding item suitable for the user. As a result, it is easier to select a bedding item easy to improve the state of sleep.

It is also preferred that the bedding item selection system of the second aspect of the invention should further include: a physical information input unit to which physical information including height and weight of the user is input; a sleep information storage unit which stores correlation data among the physical property, the degree of sound sleep, and the physical information, which are collected in advance; a test physical property recognition unit which recognizes, as a test physical property, the physical property which is likely to increase the degree of sound sleep of the user based on the input physical information and the correlation data stored in the sleep information storage unit; and a test bedding item selection unit which selects, from the multiple test bedding items, the test bedding item which is likely to increase the degree of sound sleep of the user based on the physical property recognized as the test physical property by the test physical property recognition unit and the physical property stored in the test bedding item physical property storage unit.

Thus, when the test bedding item is selected based on user's physical information input to the physical information input unit, and the correlation data among the physical property, the degree of sound sleep, and the physical information, which are stored in the sleep information storage unit, it is easy to select the test bedding item which is likely to increase the degree of sound sleep of the user.

As a result, since it is easy for suitable bedding item recognition unit to recognize, as a suitable bedding item, the test bedding item high in degree of sound sleep without repeating experimental sleeping using test bedding items many times (i.e., this makes it easier to obtain a physical property which is likely to be able to improve the state of sleep), it is easier to select a bedding item easy to improve the state of sleep.

It is further preferred that the bedding item selection system of the second aspect of the invention should be such that, when a test bedding item to be used is selected based on correlation data among the physical property, the degree of sound sleep; and the physical information, which are stored in the sleep information storage unit, the sleep information storage unit stores the degree of sound sleep input to the degree-of-sound-sleep input unit, the physical information on the user who entered the degree of sound sleep, and the physical property of the test bedding item used by the user.

Thus, when data used in selecting a bedding item are accumulated, it is easy to select a suitable test bedding item from the beginning next time the bedding item selection system is used. As a result, it is easier to select a bedding item easy to improve the state of sleep.

The bedding item selection system of the third aspect of the invention is a bedding item selection system configured to select a bedding item from multiple selectable bedding items, including: a physical information input unit to which physical information including height and weight of a user is input; a selectable bedding item physical property storage unit which stores the physical property including firmness for each of the selectable bedding items; a sleep information storage unit which stores correlation data among the physical property, a deep sleep rate, and the physical information, which are collected in advance; a suitable physical property recognition unit which recognizes, as a suitable physical property, the physical property which is likely to increase the deep sleep rate of the user based on the input physical information and the correlation data stored in the sleep information storage unit; and a bedding item selection unit which selects, from the multiple selectable bedding items, a bedding item which is likely to increase the deep sleep rate of the user based on the physical property recognized as the suitable physical property by the suitable physical property recognition unit and the physical property stored in the selectable bedding item physical property storage unit.

Thus, in the bedding item selection system of the present invention, the suitable physical property recognition unit recognizes, as the suitable physical property, the physical property which is likely to increase the deep sleep rate of the user based on user's physical information input to the physical information input unit, and the correlation data among the physical property, the deep sleep rate, and the physical information, which are stored in the sleep information storage unit. Then, the bedding item selection unit selects a bedding item based on the physical property recognized as the suitable physical property.

In other words, in the bedding item selection system of the present invention, the user's personal physical information and the physical properties including the firmness, which is easy to measure and strongly influences the state of sleep, are used in selecting a bedding item. Therefore, according to the bedding item selection system of the present invention, since a bedding item can be selected while reflecting the user's physical information in the physical property which objectively influences the sleep, a bedding item easy to improve the state of sleep can be selected.

The bedding item selection system of the fourth aspect of the invention is a bedding item selection system configured to select a bedding item from a plurality of selectable bedding items, including: a physical information input unit to which physical information including height and weight of a user is input; a selectable bedding item physical property storage unit which stores the physical property including firmness for each of the selectable bedding items; a sleep information storage unit which stores correlation data among the physical property, a degree of sound sleep, and the physical information, which are collected in advance; a suitable physical property recognition unit which recognizes, as a suitable physical property, the physical property which is likely to increase the degree of sound sleep of the user based on the input physical information and the correlation data stored in the sleep information storage unit; and a bedding item selection unit which selects, from the multiple selectable bedding items, a bedding item which is likely to increase the degree of sound sleep of the user based on the physical property recognized as the suitable physical property by the suitable physical property recognition unit and the physical property stored in the selectable bedding item physical property storage unit.

Thus, in the bedding item selection system of the present invention, the suitable physical property recognition unit recognizes, as the suitable physical property, the physical property which is likely to increase the degree of sound sleep of the user based on user's physical information input to the physical information input unit, and the correlation data among the physical property, the degree of sound sleep, and the physical information, which are stored in the sleep information storage unit. Then, the bedding item selection unit elects a bedding item based on the physical property recognized as the suitable physical property.

In other words, in the bedding item selection system of the present invention, the user's personal physical information and the physical properties including the firmness, which is easy to measure and strongly influences the state of sleep, are used in selecting a bedding item. Therefore, according to the bedding item selection system of the present invention, since a bedding item can be selected while reflecting the user's physical information in the physical property which objectively influences the sleep, a bedding item easy to improve the state of sleep can be selected.

It is preferred that the bedding item selection system of the first aspect of the invention to the fourth aspect of the invention should be such that the physical property includes rebound resilience. This is because the rebound resilience is relatively easy to measure, and strongly influences the body movement (i.e., the state of sleep) similar to the firmness.

The bedding item physical property recognition system of the fifth aspect of the invention is a bedding item physical property recognition system configured to recognize a bedding item which is likely to increase a deep sleep rate of a user, including: a plurality of test bedding items whose physical property including firmness is different from one another; a test bedding item physical property storage unit which stores the physical property for each of the test bedding items; a biological information measurement unit which measures biological information on a user during sleep on the test bedding item; a biological information recording unit which records the biological information measured by the biological information measurement unit; a deep sleep rate calculation unit which calculates the deep sleep rate of the user based on the recorded biological information; a suitable bedding item recognition unit which compares the deep sleep rate calculated for each of the test bedding items to recognize, as a suitable bedding item, the test bedding item high in the deep sleep rate of the user; and a suitable physical property recognition unit which recognizes, as a suitable physical property, the physical property high in the deep sleep rate of the user based on the test bedding item recognized as the suitable bedding item by the suitable bedding item recognition unit and the physical property stored in the test bedding item physical property storage unit.

Thus, in the bedding item physical property recognition system of the present invention, the user first tries experimental sleeping on a test bedding item whose physical properties are obtained in advance. Here, the physical properties include firmness which is easy to measure and strongly influences the body movement (i.e., the state of sleep).

Then, based on the biological information measured by the biological information measurement unit during the experimental sleep and recorded by the biological information recording unit, the deep sleep rate calculation unit calculates a deep sleep rate of the user for each of the test bedding items. Next, based on the deep sleep rate, the suitable bedding item recognition unit recognizes, as a suitable bedding item, the test bedding item high in the deep sleep rate of the user. Finally, based on the test bedding item recognized as the suitable bedding item, the suitable physical property recognition unit recognizes, as a suitable physical property, the physical property high in the deep sleep rate of the user.

In other words, in the bedding item physical property recognition system of the present invention, the physical property including firmness, which strongly influences the state of sleep is recognized based on the deep sleep rate obtained based on user's personal biological information. Therefore, according to the bedding item physical property recognition system of the present invention, since the sleep information acquired for each user is reflected in the physical property which objectively influences the sleep, the physical property of a bedding item easy to improve the state of sleep can be selected.

The bedding item physical property recognition system of the sixth aspect of the invention is a bedding item physical property recognition system configured to recognize a bedding item which is likely to increase a degree of sound sleep of a user, including: a plurality of test bedding items whose physical property including firmness is different from one another; a test bedding item physical property storage unit which stores the physical property for each of the test bedding items; a degree-of-sound-sleep input unit to which a degree of sound sleep the user feels after sleep on the test bedding item is input; a suitable bedding item recognition unit which compares the degree of sound sleep input for each of the test bedding items to recognize, as a suitable bedding item, the test bedding item high in the degree of sound sleep of the user; and a suitable physical property recognition unit which recognizes, as a suitable physical property, the physical property high in the degree of sound sleep of the user based on the test bedding item recognized as the suitable bedding item by the suitable bedding item recognition unit and the physical property stored in the test bedding item physical property storage unit.

Thus, in the bedding item physical property recognition system of the present invention, the user first tries experimental sleeping on a test bedding item whose physical properties are obtained in advance. Here, the physical property includes firmness which is easy to measure and strongly influences the body movement (i.e., the state of sleep).

Then, the user inputs, to the degree-of-sound-sleep input unit, a degree of sound sleep the user feels after the experimental sleep. Next, based on the degree of sound sleep, the suitable bedding item recognition unit recognizes, as a suitable bedding item, the test bedding item high in the degree of sound sleep of the user. Finally, based on the test bedding item recognized as the suitable bedding item, the suitable physical property recognition unit recognizes, as a suitable physical property, the physical property high in the degree of sound sleep of the user.

In other words, in the bedding item physical property recognition system of the present invention, the physical property including firmness, which strongly influences the state of sleep, is recognized based on the degree of sound sleep entered by the user. Therefore, according to the bedding item physical property recognition system of the present invention, since the sleep information acquired for each user is reflected in the physical property which objectively influences the sleep, the physical property of a bedding item easy to improve the state of sleep can be selected.

The bedding item physical property recognition system of the seventh aspect of the invention is a bedding item physical property recognition system configured to recognize a bedding item which is likely to increase a deep sleep rate of a user, including: a physical information input unit to which physical information including height and weight of the user is input; a sleep information storage unit which stores correlation data among physical property including firmness, the deep sleep rate, and the physical information, which are collected in advance; and a suitable physical property recognition unit which recognizes, as a suitable physical property, the physical property which is likely to increase the deep sleep rate of the user based on the input physical information and the correlation data stored in the sleep information storage unit.

Thus, in the bedding item physical property recognition system of the present invention, the suitable physical property recognition unit recognizes, as a suitable physical property, the physical property which is likely to increase the deep sleep rate of the user based on user's physical information input to the physical information input unit, and the correlation data among the physical property, the deep sleep rate, and the physical information, which are stored in the sleep information storage unit.

In other words, in the bedding item physical property recognition system of the present invention, each of the physical property including firmness, which strongly influences the state of sleep, is recognized based on user's personal physical information. Therefore, according to the bedding item physical property recognition system of the present invention, since the user's physical information is reflected in the physical property which objectively influences the sleep, the physical property of a bedding item easy to improve the state of sleep can be selected.

The bedding item physical property recognition system of the eighth aspect of the invention is a bedding item physical property recognition system configured to recognize a bedding item which is likely to increase a degree of sound sleep of a user, including: a physical information input unit to which inputs physical information including height and weight of the user is input; a sleep information storage unit which stores correlation data among the physical property including firmness, the degree of sound sleep, and the physical information, which are collected in advance; and a suitable physical property recognition unit which recognizes, as a suitable physical property, the physical property which is likely to increase the degree of sound sleep of the user based on the input physical information and the correlation data stored in the sleep information storage unit.

Thus, in the bedding item physical property recognition system of the present invention, the suitable physical property recognition unit recognizes, as a suitable physical property, the physical property which is likely to increase the degree of sound sleep of the user based on user's physical information input by the physical information input unit, and the correlation data among the physical property, the degree of sound sleep, and the physical information, which are stored in the sleep information storage unit.

In other words, in the bedding item physical property recognition system of the present invention, the physical property including firmness, which strongly influences the state of sleep, is recognized based on user's personal physical information. Therefore, according to the bedding item physical property recognition system of the present invention, since the user's physical information is reflected in the physical property which objectively influences the sleep, the physical property of a bedding item easy to improve the state of sleep can be selected.

BRIEF DESCRIPTION OF DRAWINGS

FIG. 3 is a schematic diagram of a screen displayed when a user enters physical information on a tablet in the bedding item selection system of FIG. 1.

FIG. 4 is a schematic diagram illustrating an example of a data table of correlation data among physical information, the deep sleep rate and the degree of sound sleep, and the physical property of each test bedding item in the bedding item selection system of FIG. 1.

FIG. 7 is a schematic diagram illustrating a schematic configuration of a bedding item selection system according to a second embodiment.

FIG. 8 is a flowchart illustrating processing performed by the bedding item selection system of FIG. 7 in a bedding item selection process.

DESCRIPTION OF EMBODIMENTS

First Embodiment

Referring to FIG. 1 to FIG. 6, a bedding item selection system according to a first embodiment will be described below. The bedding item selection system of the embodiment is related to the first aspect of the invention and second aspect of the invention mentioned above, and includes the bedding item physical property recognition system according to the fifth aspect of the invention and sixth aspect of the invention.

Figure 1:
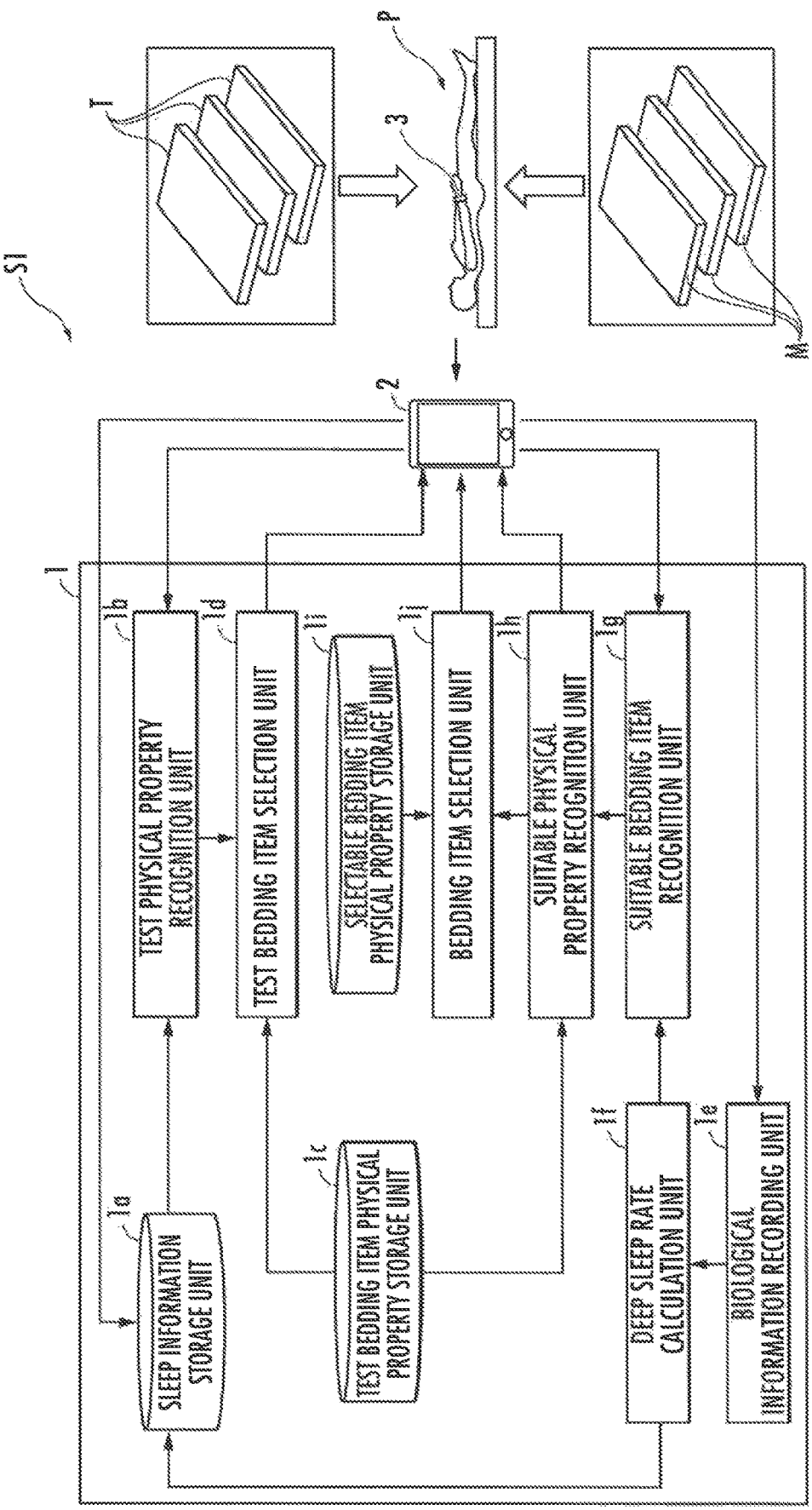
FIG. 1 is a schematic diagram illustrating a schematic configuration of a bedding item selection system according to a first embodiment.

Referring first to FIG. 1, the configuration of a bedding item selection system S1 will be described.

As illustrated in FIG. 1, the bedding item selection system S1 includes a server 1 managed by a bedding item dealer, a tablet 2 placed in the home of user P, a sensor 3 which measures biological information on the user P, and multiple test bedding items T and multiple selectable bedding items M prepared in a warehouse or the like of a bedding item retail store. The server 1 and the tablet 2 are connected through a network.

The server 1 is an information processing terminal including a CPU, a memory, and the like. The server 1 has a sleep information storage unit 1a which stores sleep information collected in advance, a test physical property recognition unit 1b which recognizes the physical properties of test bedding items used in experimental sleeping, a test bedding item physical property storage unit 1c which stores the physical properties of test bedding items, and a test bedding item selection unit 1d which selects a test bedding item used in experimental sleeping.

The sleep information stored in the sleep information storage unit 1a is correlation data among the physical properties of bedding items, the deep sleep rate or the degree of sound sleep, and physical information, which are collected in advance. The correlation data are updated based on information from the tablet 2 and a deep sleep rate calculation unit 1f to be described later.

Based on the physical information on the user P entered on the tablet 2 and the correlation data stored in the sleep information storage unit 1a, the test physical property recognition unit 1b recognizes, as a test physical property, a physical property which is likely to increase the deep sleep rate and the degree of sound sleep of the user P.

The test bedding item physical property storage unit 1c stores the physical property for each test bedding item T.

Based on the physical properties recognized by the test physical property recognition unit 1b as the test physical properties, and the physical properties stored in the test bedding item physical property storage unit 1c, the test bedding item selection unit 1d selects, from the multiple test bedding items T, a test bedding item which is likely to increase the deep sleep rate and the degree of sound sleep of the user P.

The server 1 further has a biological information recording unit 1e which records biological information transmitted from the sensor 3, the deep sleep rate calculation unit 1f which calculates the deep sleep rate of the user P, a suitable bedding item recognition unit 1g which recognizes a bedding item suitable for the user P from the multiple test bedding items T, a suitable physical property recognition unit 1h which recognizes a physical property suitable for the user a selectable bedding item physical property storage unit 1i which stores the physical properties of the selectable bedding items M, and a bedding item selection unit 1j which selects a bedding item to be offered to the user P.

The biological information recording unit 1e receives and records, through the tablet 2, biological information measured by the sensor 3 during experimental sleeping of the user P on a test bedding item T.

Based on information recorded in the biological information recording unit 1e, the deep sleep rate calculation unit 1f calculates the deep sleep rate of the user P for each test bedding item T.

Here, the deep sleep rate means the rate of deep sleep during the total sleep time. Further, the term "deep sleep" means the state of sleep stages 3 and 4 in non-REM sleep (i.e., the state of slow-wave sleep).

The suitable bedding item recognition unit 1g, compares the deep sleep rate calculated for each test bedding item T with the degree of sound sleep input on the tablet 2 to recognize, as a suitable bedding item, the test bedding item high in deep sleep rate and degree of sound sleep of the user.

Based on the test bedding item T recognized by the suitable bedding item recognition unit 1g as the suitable bedding item, and the physical property of the test bedding item T stored in the test bedding item physical property storage unit 1c, the suitable physical property recognition unit 1h recognizes, as a suitable physical property, a physical property high in deep sleep rate and degree of sound sleep of the user P.

The selectable bedding item physical property storage unit 1i stores the physical property for each selectable bedding item M.

Based on the physical property recognized by the suitable physical property recognition unit 1h as the suitable physical property, and the physical properties of selectable bedding items M stored in the selectable bedding item physical property storage unit 1i, the bedding item selection unit 1j selects, from the multiple selectable bedding items M, a bedding item high in deep sleep rate and degree of sound sleep of the user P.

The tablet 2 (physical information input unit, degree-of-sound-sleep input unit) has an input/output unit 2a (see FIG. 3). The user P enters, through the input/output unit 2a, own physical information and the degree of sound sleep the user feels after sleeping on the test bedding item T, and checks on the test bedding item T and the selectable bedding items M displayed on the input/output unit 2a.

Here, the degree of sound sleep means a degree of whether the user P feels that the user slept well after the sleeping, which is a subjective point of view. The degree of sound sleep is expressed at five levels from "1" indicative of a feeling of the most troubled sleep to "5" indicative of a feeling of being slept best. However, the degree of sound sleep may be expressed at four levels or less, or at six levels or more.

Here, the physical information includes sex and age in addition to height and weight. The correlation data stored in the sleep information storage unit 1a are data in which these pieces of physical information are made corresponding to the physical property of each bedding item, and the deep sleep rate and the degree of sound sleep.

In the bedding item selection system S1, the tablet 2 is used as the physical information input unit and the degree-of-sound-sleep input unit to enable the user P to enter the physical information and the degree of sound sleep easily at home. However, the physical information input unit and the degree-of-sound-sleep input unit of the present invention may be any other terminal such as a PC as long as the physical information and the degree of sound sleep can be entered. Further, the installation site is not limited to the home of user P, it may be the front of a bedding item retail store, or the like.

The sensor 3 (biological information measurement unit) measures biological information on the user P during sleep on the test bedding item, and transmits the biological information to the biological information recording unit 1e of the server 1 through the tablet 2. The biological information measured by the sensor 3 may be any information as long as it can calculate the deep sleep rate. For example, the biological information may be brain wave changes, changes in heart rate, changes in respiration, or the number of body movements during the sleep of the user P.

The multiple test bedding items T are different from one another in terms of the physical property. Each test bedding item is numbered, and the physical property of the test bedding item is stored for each number of the test bedding item in the test bedding item physical property storage unit 1c.

The multiple selectable bedding items M are different from one another in terms of the physical property. Each selectable bedding item is numbered, and the physical property of the selectable bedding item is stored for each number of the selectable bedding item in the selectable bedding item physical property storage unit 1i.

Here, the bedding items in the bedding item selection system S1 include bedding items located below the body of the user P during sleeping, such as a pillow, a mattress, a huggable pillow, as well as a futon mattress. The physical properties include the heat-retaining property, the moisture absorption-desorption property, the material (texture), and the like, in addition to the firmness and the rebound resilience. Although only the firmness will be described below, the other physical properties are used as the determination criteria like the firmness to select a test bedding item T or a selectable bedding item M in the bedding item selection system S1.

Note that the bedding items of the present invention are not necessarily limited to those mentioned above, and the bedding items may also include a coverlet, pajamas, and the like. Then, when these are set as selectable bedding items, physical properties easy to measure in the bedding items and important to sleeping may be used as criteria. For example, when a coverlet and pajamas are set as selectable bedding items, heat-retaining property, moisture absorption-desorption property, material (texture), weight, drape property, and the like may be used as criteria.

Further, the physical properties of bedding items of the present invention are not necessarily limited to those mentioned above. When the bedding item is a futon mattress, at least firmness may be included.

Figure 2:
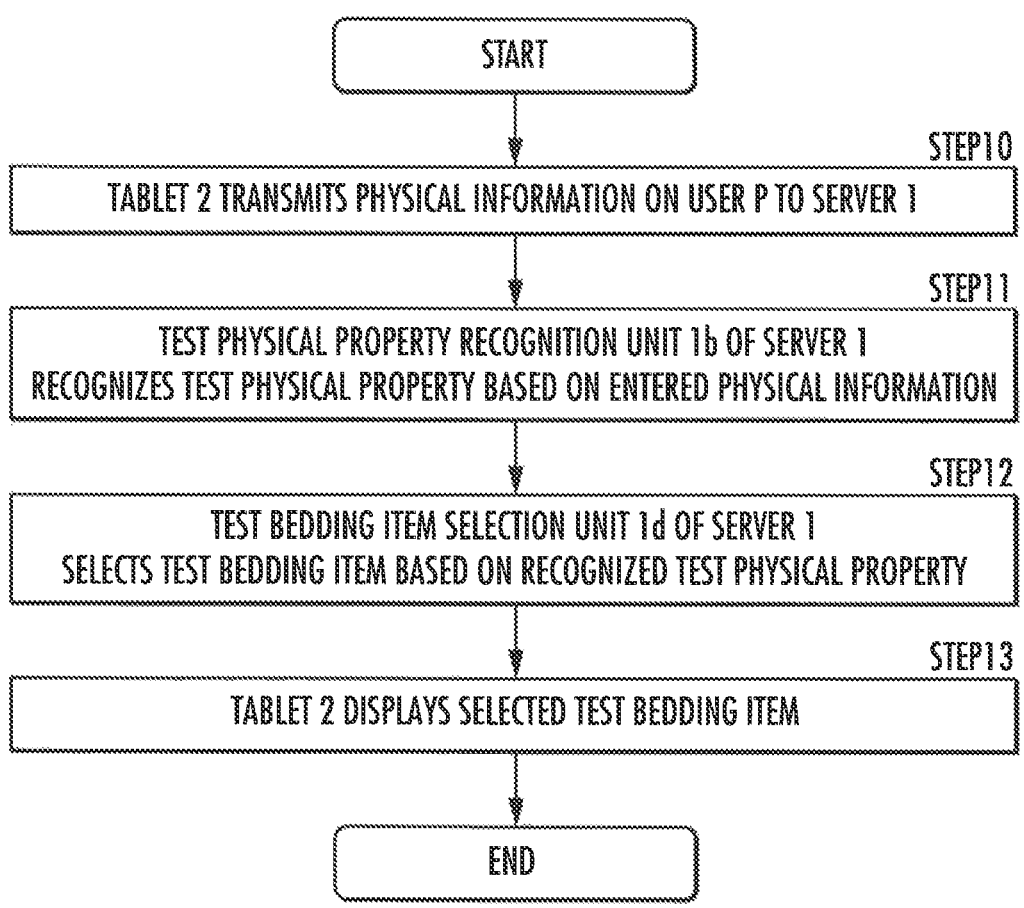
FIG. 2 is a flowchart illustrating processing performed by the bedding item selection system of FIG. 1 in a test bedding item selection process.

Referring next to FIG. 1 to FIG. 4, processing performed by the bedding item selection system S1 in a test bedding item selection process will be described. Note that FIG. 2 is a flowchart illustrating processing performed in the test bedding item selection process.

First, the tablet 2 transmits, to the server 1, physical information on the user P input by the user P to the input/output unit 2a of the tablet 2 (FIG. 2/STEP 10).

Specifically, as illustrated in FIG. 3, own name, sex, age, height, and weight are input as physical information to the input/output unit 2a of the tablet 2. The input physical information is transmitted to the test physical property recognition unit 1b of the server 1 through a network.

Next, based on the physical information received by the test physical property recognition unit 1b of the server 1, a physical property which is likely to increase the deep sleep rate and the degree of sound sleep of the user P is retrieved from the sleep information storage unit 1a, and the retrieved physical property is recognized as a test physical property (FIG. 2/STEP 11).

Specifically, based on the physical information received, the test physical property recognition unit 1b refers, for each target site (i.e., the area of each bedding item which is in contact with the body of the user P during sleep), to the correlation data among the physical property, the deep sleep rate or the degree of sound sleep, and the physical information, which are collected in advance and stored in the sleep information storage unit 1a, to search for a physical property which is likely to increase the deep sleep rate and the degree of sound sleep of the user P.

In the correlation data, as illustrated in FIG. 4, an average deep sleep rate and an average degree of sound sleep are made corresponding to a BMI value calculated from the height and the weight for each sex, age, and target site, and the physical property such as the firmness. In addition to the firmness, the physical properties include rebound resilience, air permeability, weight, material (texture and the like. Further, hip, head, shoulders, and the like are included as target sites.

Next, the test bedding item selection unit 1d of the server 1 retrieves, from the test bedding item physical property storage unit 1c, a physical property matching with or close to the recognized test physical property to select, from the multiple test bedding items T, a test bedding item T used by the user P in experimental sleeping based on the retrieval result, and transmit information on the test bedding item T to the tablet 2 (FIG. 2/STEP 12).

The physical property of the test bedding item T includes the same item as the correlation data stored in the sleep information storage unit 1a for each number assigned to each of the test bedding items T. Specifically, the firmness, the rebound resilience, or the like is included for each target site.

Although the physical properties are acquired for respective target sites, the levels of importance of these physical properties vary from target site to target site. Therefore, in the bedding item selection system S1, some test bedding items T are selected from all the test bedding items T based on a physical property acquired by setting, as the target site, the hip which is the highest in level of importance, and after that, a test bedding item T to be offered to the user P is selected from the selected test bedding items T based on a physical property acquired by setting, as the target site, the head or the shoulders, which is relatively low in level of importance.

Finally, the tablet 2 displays the selected test bedding item T (FIG. 2/STEP 13).

Based on the displayed result, the user P and the bedding item dealer make arrangements (delivery of the test bedding item T, and the like) for the user P to try experimental sleeping.

Note that the selected test bedding item T does not necessarily have to be displayed on the tablet 2, and it is only necessary for the user P to be able to try experimental sleeping using the selected test bedding item T. For example, the selected test bedding item T may be delivered to the home of the user P automatically based on the selection result.

STEP 10 to STEP 13 mentioned above are the test bedding item selection process in the bedding item selection system S1.

Thus, in the bedding item selection system S1, a test bedding item T is selected based on the physical information on the user P input through the physical information input unit, and the correlation data among the physical property, the deep sleep rate or the degree of sound sleep, and the physical information, which are stored in the sleep information storage unit 1a. Therefore, according to the bedding item selection system S1, a test bedding item T which is likely to increase the deep sleep rate and the degree of sound sleep of the user P is easily selected.

As a result, it is easy for the suitable bedding item recognition unit 1g of the server 1 to recognize a suitable bedding item high in deep sleep rate and degree of sound sleep without repeating experimental sleeping using test bedding items T many times this makes it easier to obtain a physical property which is likely to improve the state of sleep).

Note that the bedding item selection system of the present invention does not necessarily have to select a test bedding item T by the above-mentioned test bedding item selection process, and the test bedding item T may be selected by any other method. Further, when the number of kinds of test bedding items T is small and experimental sleeping is tried by using all the test bedding items T, there is no need to select a test bedding item T.

Figure 5:
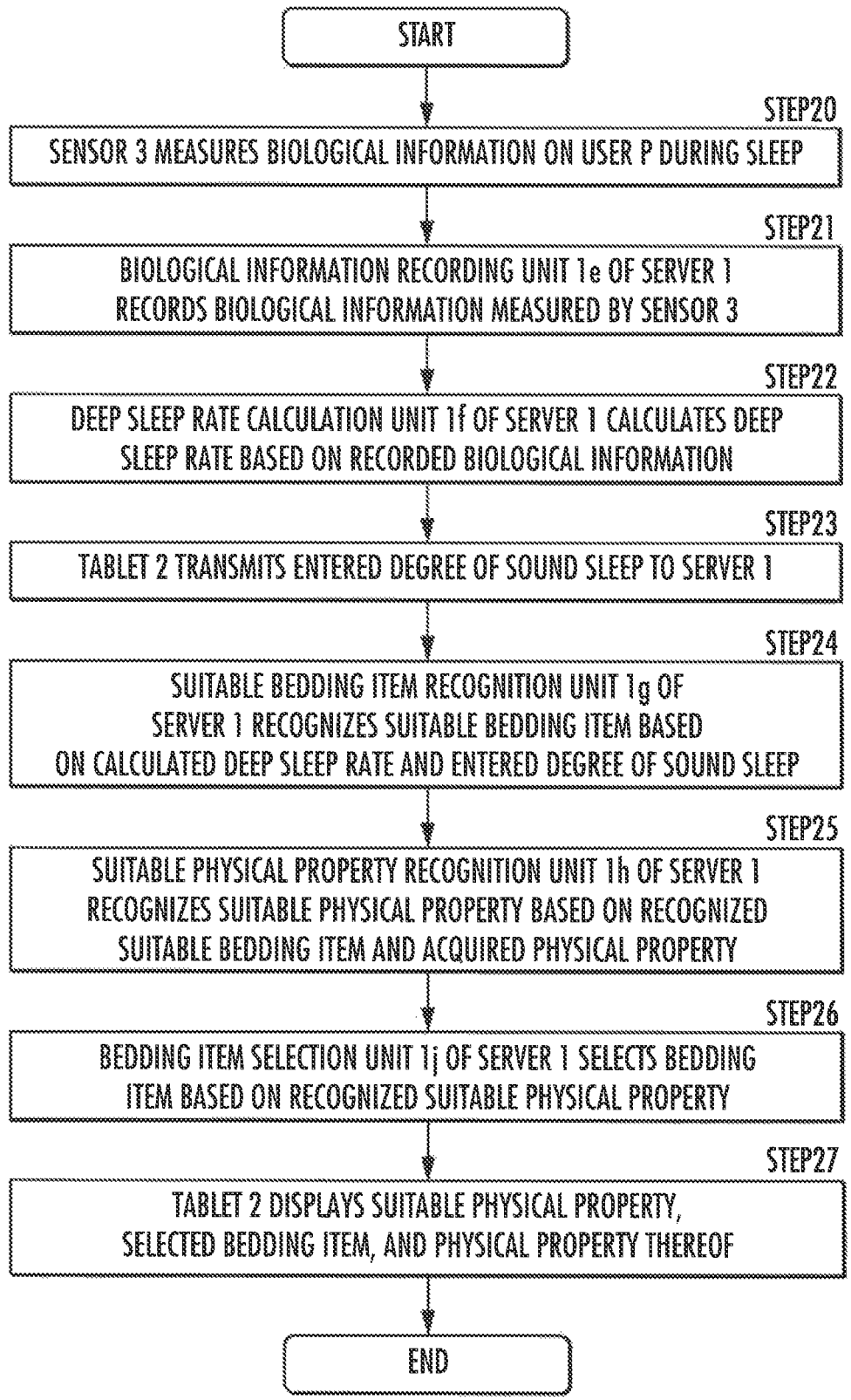
FIG. 5 is a flowchart illustrating processing performed by the bedding item selection system of FIG. 1 in a bedding item selection process.

Referring next to FIG. 1 and FIG. 5, processing performed by the bedding item selection system S1 in a bedding item selection process will be described. FIG. 5 is a flowchart illustrating the processing performed in the bedding item selection process.

First, the user P tries experimental sleeping using the selected test bedding item T. During the sleeping, the sensor 3 measures biological information on the user P during sleep using the selected test bedding item T in the test bedding item selection process, and transmits the biological information to the biological information recording unit 1e of the server 1 through the tablet 2 (FIG. 5/STEP 20).

The biological information measured here may be any data capable of calculating the deep sleep rate, such as brain wave changes, changes in heart rate, changes in respiration, or the number of body movements during the sleep of the user P.

Next, the biological information recording unit 1e of the server 1 records the biological information measured by the sensor 3 and transmitted through the tablet 2 (FIG. 5/STEP 21).

Next, the deep sleep rate calculation unit if of the server 1 calculates a deep sleep rate of the user P on the selected test bedding item T based on the biological information recorded by the biological information recording unit 1e (FIG. 5/STEP 22).

Specifically, the time of deep sleep of the user P is calculated based on the biological information, and a deep sleep rate (the rate of deep sleep during the total sleep time) is calculated based on the calculated time and the total sleep time of the user P in experimental sleeping.

Next, the user P determines, from five levels (from numerical values of 1 to 5), a degree of sound sleep the user feels after experimental sleeping using the test bedding item T, and enters the degree of sound sleep on the tablet 2. Then, the tablet 2 transmits, to the server 1, the degree of sound sleep entered by the user P (FIG. 5/STEP 23).

Note that, in the bedding item selection system S1, the entered degree of sound sleep is transmitted after the calculation of the deep sleep rate (FIG. 5/STEP 22), but the transmission may be performed simultaneously with or before the calculation of the deep sleep rate.

Next, based on the deep sleep rate calculated by the deep sleep rate calculation unit if and the degree of sound sleep entered on the tablet 2, the suitable bedding item recognition unit 1g of the server 1 recognizes, as a suitable bedding item, a test bedding item T high in both the deep sleep rate and the degree of sound sleep of the user P (FIG. 5/STEP 24).

The determination of whether the deep sleep rate and the degree of sound sleep are high or not is made, for example, by comparing the deep sleep rate, calculated for one test bedding item T or a predetermined number of test bedding items T, and the entered degree of sound sleep with predefined given values. In other words, in the bedding item selection system S1, when both the deep sleep rate and the degree of sound sleep are lower than the given values, experimental sleeping using test bedding items T is repeated until a test bedding item T for which both the deep sleep rate and the degree of sound sleep are determined to be the given values is found.

When the number of kinds of test bedding items T is small, or the like, experimental sleeping may be tried by using all the test bedding items T. In this case, a comparison of the deep sleep rate calculated for each test bedding item T and the entered degree of sound sleep with each other may be made, rather than the comparison of the calculated deep sleep rate and the entered degree of sound sleep with the given values.

Further, if the user P is satisfied, experimental sleeping may be completed after one try. Conversely, when the user P is not satisfied, experimental sleeping using any other test bedding item may be continued even if the deep sleep rate and the degree of sound sleep are higher than the given values.

Next, the suitable physical property recognition unit 1h retrieves, from physical properties stored in the test bedding item physical property storage unit 1c, the physical property of the test bedding item recognized as a suitable bedding item by the suitable bedding item recognition unit Ig, recognizes the retrieved physical property as a suitable physical property, and transmits the suitable physical property to the tablet 2 (FIG. 5/STEP 25).

Next, the bedding item selection unit 1j of the server 1 retrieves, from the selectable bedding item physical property storage unit 1i, a physical property matching with or close to the recognized test physical property to select, from the multiple selectable bedding items M, a bedding item to be offered to the user P based on the retrieval result, and transmit information on the bedding item to the tablet 2 (FIG. 5/STEP 26).

The physical property of each of the selectable bedding items M includes the same item as the correlation data stored in the sleep information storage unit 1*a* for each number assigned to each of the selectable bedding items M. Specifically, the firmness, the rebound resilience, or the like is included for each target site.

Although the physical property is acquired for each target site, the level of importance of the physical property varies from target site to target site. Therefore, in the bedding item selection system S1, some selectable bedding items M are selected from all the selectable bedding items M based on the physical property acquired by setting, as the target site, the hip which is the highest in level of importance, and after that, a selectable bedding item M to be offered to the user P is selected from the selected selectable bedding items M based on a physical property acquired by setting, as the target site, the head or the shoulders, which is relatively low in level of importance.

Finally, the tablet 2 displays the suitable physical property for each target site, and the selected selectable bedding item M and the physical property thereof for each target site (FIG. 5/STEP 27).

Note that the physical properties do not necessarily have to be divided by target site, and one physical property may be set for one bedding item. Further, the physical properties do not have to be displayed on the tablet 2, and only the selectable bedding items M may be displayed.

STEP 20 to STEP 27 mentioned above are the bedding item selection process in the bedding item selection system S1.

Figure 6:
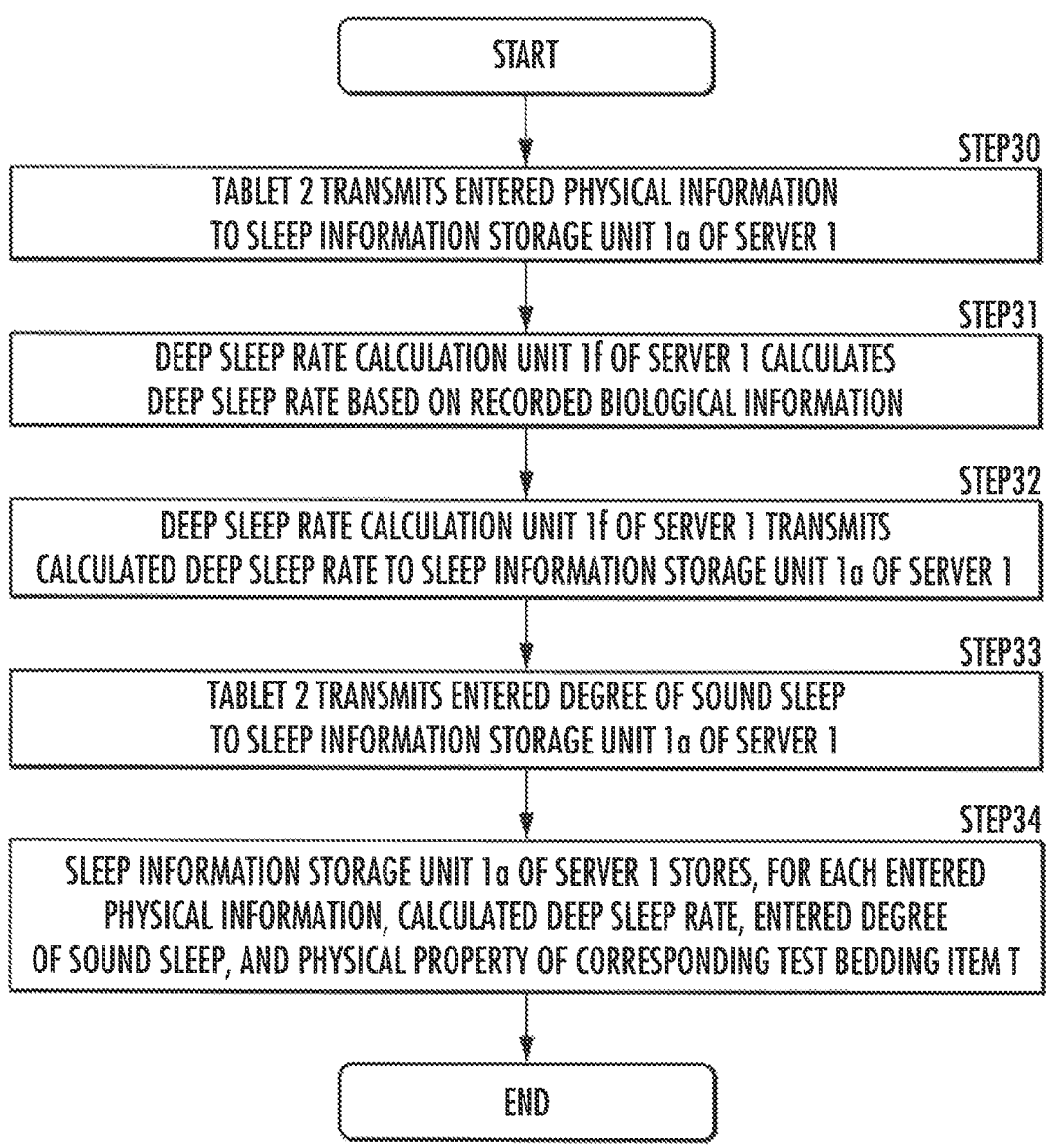
FIG. 6 is a flowchart illustrating processing performed by the bedding item selection system of FIG. 1 in an information collection process.

Referring next to FIG. 1 and FIG. 6, processing performed by the bedding item selection system S1 in an information collection process will be described. FIG. 6 is a flowchart illustrating the processing performed in the information collection process.

This information collection process is executed simultaneously with the test bedding item selection process and the bedding item selection process mentioned above.

First, the tablet 2 transmits, to the sleep information storage unit 1*a* of the server 1, physical information on the user P input by the user P to the input/output unit 2*a* of the tablet 2 (FIG. 6/STEP 30).

The sleep information storage unit 1*a* temporarily stores the physical information.

Next, based on the biological information measured by the sensor 3 and recorded by the biological information recording unit 1*e* of the server 1, the deep sleep rate calculation unit 1*f* of the server 1 calculates a deep sleep rate of the user P on the selected test bedding item T (FIG. 6/STEP 31).

Next, the deep sleep rate calculation unit 1*f* of the server 1 transmits the calculated deep sleep rate to the sleep information storage unit 1*a* of the server 1 (FIG. 6/STEP 32).

The sleep information storage unit 1*a* temporarily stores the received deep sleep rate in such a manner as to correspond to the physical information on the user P stored in advance.

Next, the tablet 2 transmits, to the sleep information storage unit 1*a* of the server 1, the degree of sound sleep entered by the user P (FIG. 6/STEP 33).

The sleep information storage unit 1*a* temporarily stores the received degree of sound sleep in such a manner as to correspond to the physical information on the user P stored in advance.

Finally, the sleep information storage unit 1*a* of the server 1 stores, for each piece of physical information temporarily stored, the calculated deep sleep rate, the entered degree of sound sleep, and the physical property of a corresponding test bedding item T (i.e., the test bedding item T used in experimental sleeping when the deep sleep rate is calculated and the degree of sound sleep is entered) (FIG. 6/STEP 34).

STEP 30 to STEP 34 mentioned above are the information collection process in the bedding item selection system S1.

Thus, in the bedding item selection system S1, experimental sleeping is done to collect correlation data between the deep sleep rate obtained based on personal biological information on the user P and the physical properties including the firmness which is easy to measure and strongly influences the state of sleep, and correlation data between the degree of sound sleep entered by the user individually and the physical properties including the firmness which is easy to measure and strongly influences the state of sleep.

Therefore, according to the bedding item selection system S1, since sleep information acquired for each user P is collected while making the sleep information corresponding to physical properties having actual influences on the sleep, reliable sleep information can be collected.

Then, in the bedding item selection system S1, since data are thus accumulated, it is easy to select an appropriate test bedding item T from the beginning when the bedding item selection system S1 is used next time. As a result, it is easy to select a bedding item which is more likely to improve the state of sleep.

When sufficient data are already accumulated or information is collected by any other method, the above information collection process may be omitted.

As described above, in the bedding item selection system S1, the deep sleep rate obtained based on the personal biological information on the user P, the degree of sound sleep entered by the user P, and physical properties including the firmness and the rebound resilience, which are easy to measure and strongly influence the state of sleep, are used to select a bedding item and the physical properties thereof. Therefore, according to the bedding item selection system S1, since a bedding item can be selected while reflecting the sleep information acquired for each user P in the physical properties which objectively influence the sleep, a bedding item easy to improve the state of sleep and the physical property thereof can be selected.

Second Embodiment

Referring to FIG. 7 and FIG. 8 below, a bedding item selection system according to a second embodiment will be described. The bedding item selection system of the embodiment is related to the third aspect of the invention and fourth aspect of the invention mentioned above, and includes the bedding item physical property recognition system according to the seventh aspect of the invention and eighth aspect of the invention.

A bedding item selection system S2 of this embodiment is different from the bedding item selection system S1 of the first embodiment in the configuration of a processing section included in a server and processing performed on the server, and the presence or absence of a sensor to measure user's biological information.

Therefore, only the configuration of the processing section included in the server of the embodiment and the processing performed on the server will be described in detailed below. The same reference numerals as those in the first embodiment are given to the other components to omit detailed description thereof.

Referring first to FIG. 7, the configuration of the bedding item selection system S2 will be described.

As illustrated in FIG. 7, the bedding item selection system S2 includes a server 4 managed by a bedding item dealer, the tablet 2 placed in a bedding item retail store, and multiple selectable bedding items M prepared in a warehouse or the like of the bedding item retail store. The server 4 and the tablet 2 are connected through a network.

The server 4 is an information processing terminal including a CPU, a memory, and the like. The server 4 has a sleep information storage unit 4a which stores sleep information collected in advance, a suitable physical property recognition unit 4b which recognizes physical properties suitable for the user P, a selectable bedding item physical property storage unit 4c which stores the physical properties of selectable bedding items M, and a bedding item selection unit 4d which selects a bedding item to be offered to the user P.

The sleep information stored in the sleep information storage unit 4a is correlation data among the physical properties of bedding items, the deep sleep rate or the degree of sound sleep, and physical information, which are collected in advance.

Based on the physical information entered on the tablet 2 and the correlation data stored in the sleep information storage unit 4a, the suitable physical property recognition unit 4b recognizes, as a suitable physical property, a physical property which is likely to increase the deep sleep rate and the degree of sound sleep of the user P.

The selectable bedding item physical property storage unit 4c stores the physical property for each of the selectable bedding items M.

Based on the physical properties recognized by the suitable physical property recognition unit 4b as the suitable physical properties, and the physical properties of the selectable bedding items M stored in the selectable bedding item physical property storage unit 4c, the bedding item selection unit 4d selects, from the multiple electable bedding items M, a bedding item high in deep sleep rate and degree of sound sleep of the user P.

The tablet 2 (physical information input unit, degree-of-sound-sleep input unit) has the input/output unit 2a (see FIG. 3). The user P enters own physical information through the input/output unit 2a, and checks on the selectable bedding items M displayed on the input/output unit 2a.

The multiple selectable bedding items M are different from one another in terms of the physical property. A number is assigned to each selectable bedding item, and the physical property of each electable bedding item is stored in the selectable bedding item physical property storage unit 1i for each number of the selectable bedding item.

Referring next to FIG. 8, processing performed by the bedding item selection system S2 in a bedding item selection process will be described. FIG. 8 is a flowchart illustrating the processing performed in the bedding item selection process.

First, the tablet 2 transmits, to the server 1, physical information on the user P input by the user P to the input/output unit 2a of the tablet 2 (FIG. 8/STEP 40).

Specifically, own name, sex, age, height, and weight are input as physical information to the input/output unit of the tablet 2. The input physical information is transmitted to the suitable physical property recognition unit 4b of the server 4 through a network.

Next, based on the received physical information, the suitable physical property recognition unit 4b of the server 4 retrieves, from the sleep information storage unit 4a, a physical property which is likely to increase the deep sleep rate and the degree of sound sleep of the user P, and recognizes the retrieved physical property as a suitable physical property (FIG. 8/STEP 41).

Specifically, based on the received physical information, the suitable physical property recognition unit 4b refers, for each target site (i.e., the area of each bedding item which is in contact with the body of the user P during sleep), to the correlation data among the physical property, the deep sleep rate or the degree of sound sleep, and the physical information, which are collected in advance and stored in the sleep information storage unit 4a, to search for a physical property which is likely to increase the deep sleep rate and the degree of sound sleep of the user P.

Next, the bedding item selection unit 4d of the server 4 retrieves, from the multiple selectable bedding item M physical property storage unit 4c, a physical property matching with or close to the recognized suitable physical property to select a bedding item to be offered to select, from the multiple selectable bedding items M, a bedding item to be offered to the user P based on the retrieval result, and transmit information on the bedding item to the tablet 2 (FIG. 8/STEP 42).

Finally, the tablet 2 displays the suitable physical property and the selected bedding item (FIG. 8/STEP 43).

As described above, in the bedding item selection system S2, the personal biological information on the user P and the physical properties including the firmness which is easy to measure and strongly influences the state of sleep are used to select a bedding item and the physical properties thereof. Therefore, according to the bedding item selection system S2, since a bedding item can be selected while reflecting the user's physical information in the physical properties which objectively influence the sleep, a bedding item easy to improve the state of sleep and the physical property thereof can be selected.

Other Embodiments

The embodiments illustrated in the drawings are described above, but the present invention is not limited to these forms.

For example, in the aforementioned embodiments, various information processing is performed in the processing sections included in the server 1 and server 4. However, the information processing does not necessary have to be performed on each server. For example, the terminal to process data may be changed appropriately, such as to perform part of the processing on the tablet.

Further, in the aforementioned embodiments, the rebound resilience and the like are included as the physical properties, in addition to the firmness, used in selecting a bedding item. However, when the bedding item is a bedding item located below the body of the user P during sleeping, such as a futon mattress, since it is enough to include at least the firmness as the physical property, the rebound resilience may be excluded from the physical properties used to select a bedding item. Conversely, any physical property other than that illustrated in the aforementioned embodiments may be used as the physical property used to select a bedding item.

Further, in the aforementioned embodiments, the deep sleep rate and the degree of sound sleep are used as the criteria to select a bedding item. However, both of them do not necessarily have to be used, and either one of the deep sleep rate and the degree of sound sleep may be used as a criterion.

DESCRIPTION OF REFERENCE NUMERALS 1, 4 . . . server, 1a, 4a . . . sleep information storage unit, 1b . . . test physical property recognition unit, 1c . . . test bedding item physical property storage unit, 1d . . . test bedding item selection unit, 1e . . . biological information recording unit, 1f . . . deep sleep rate calculation unit, 1g . . . suitable bedding item recognition unit, 1h, 4b . . . suitable physical property recognition unit, 1i, 4c . . . selectable bedding item physical property storage unit, 1j, 4d . . . bedding item selection unit, 2 . . . tablet (physical information input unit, degree-of-sound-sleep input unit), 2a . . . input/output unit, 3 . . . sensor (biological information measurement unit), M . . . selectable bedding item, P . . . user, S1, S2 . . . bedding item selection system, T . . . test bedding item.

The invention claimed is:

1. A bedding item selection system configured to select a bedding item from a plurality of selectable bedding items, comprising:
a plurality of test bedding items whose physical property including firmness is different from one another;
a selectable bedding item physical property storage unit which stores the physical property for each of the selectable bedding items;
a test bedding item physical property storage unit which stores the physical property for each of the test bedding items;
a biological information measurement unit which measures biological information on a user during sleep on the test bedding item;
a biological information recording unit which records the biological information measured by the biological information measurement unit;
a deep sleep rate calculation unit which calculates a deep sleep rate of the user based on the recorded biological information;
a suitable bedding item recognition unit which compares the deep sleep rate calculated for each of the test bedding items to recognize, as a suitable bedding item, the test bedding item high in the deep sleep rate of the user;
a suitable physical property recognition unit which recognizes, as a suitable physical property, a physical property high in the deep sleep rate of the user based on the test bedding item recognized as the suitable bedding item by the suitable bedding item recognition unit and the physical property stored in the test bedding item physical property storage unit; and
a bedding item selection unit which selects, from the plurality of selectable bedding items, a bedding item high in the deep sleep rate of the user based on the physical property recognized as the suitable physical property by the suitable physical property recognition unit and the physical property stored in the selectable bedding item physical property storage unit.

2. The bedding item selection system according to claim 1, further comprising a degree-of-sound-sleep input unit to which a degree of sound sleep the user feels after sleep on the test bedding item is input,
wherein the suitable bedding item recognition unit compares the deep sleep rate calculated for each of the test bedding items and the input degree of sound sleep to recognize, as the suitable bedding item, the test bedding item high in the deep sleep rate and the degree of sound sleep of the user,
the suitable physical property recognition unit recognizes, as the suitable physical property, the physical property high in the deep sleep rate and the degree of sound sleep of the user based on the test bedding item recognized as the suitable bedding item by the suitable bedding item recognition unit and the physical property stored in the test bedding item physical property storage unit, and
the bedding item selection unit selects, from the plurality of selectable bedding items, a bedding item high in the deep sleep rate and the degree of sound sleep of the user.

3. The bedding item selection system according to claim 1, further comprising:
a physical information input unit to which physical information including height and weight of the user is input;
a sleep information storage unit which stores correlation data among the physical property, the deep sleep rate, and the physical information, which are collected in advance;
a test physical property recognition unit which recognizes, as a test physical property, the physical property which is likely to increase the deep sleep rate of the user based on the input physical information and the correlation data stored in the sleep information storage unit; and
a test bedding item selection unit which selects, from the plurality of test bedding items, the test bedding item which is likely to increase the deep sleep rate of the user based on the physical property recognized as the test physical property by the test physical property recognition unit and the physical property stored in the test bedding item physical property storage unit.

4. The bedding item selection system according to claim 3, wherein the sleep information storage unit stores the deep sleep rate calculated by the deep sleep rate calculation unit, the physical information on the user whose deep sleep rate is calculated, and the physical property of the test bedding item used by the user.

5. The bedding item selection system according to claim 1, wherein the physical property includes rebound resilience.

6. A bedding item physical property recognition system configured to recognize a bedding item which is likely to increase a deep sleep rate of a user, comprising:
a plurality of test bedding items whose physical property including firmness is different from one another;
a test bedding item physical property storage unit which stores the physical property for each of the test bedding items;
a biological information measurement unit which measures biological information on a user during sleep on the test bedding item;
a biological information recording unit which records the biological information measured by the biological information measurement unit;
a deep sleep rate calculation unit which calculates the deep sleep rate of the user based on the recorded biological information;

a suitable bedding item recognition unit which compares the deep sleep rate calculated for each of the test bedding items to recognize, as a suitable bedding item, the test bedding item high in the deep sleep rate of the user; and
a suitable physical property recognition unit which recognizes, as a suitable physical property, the physical property high in the deep sleep rate of the user based on the test bedding item recognized as the suitable bedding item by the suitable bedding item recognition unit and the physical property stored in the test bedding item physical property storage unit.

\* \* \* \* \*